United States Patent [19]

Yamamoto

[11] Patent Number: 5,766,940
[45] Date of Patent: Jun. 16, 1998

[54] PLASMID AND PLASMID VECTOR

[75] Inventor: Naoyuki Yamamoto, Sagamihara, Japan

[73] Assignee: The Calpis Food Industry Co., Ltd., Tokyo, Japan

[21] Appl. No.: 795,345

[22] Filed: Feb. 4, 1997

[30] Foreign Application Priority Data

Feb. 9, 1996 [JP] Japan ................... 8-023651

[51] Int. Cl.$^6$ .................................................. C12N 15/00
[52] U.S. Cl. ............................................................ 435/320.1
[58] Field of Search .......................................... 435/320.1

[56] References Cited

PUBLICATIONS

Fortina, M.G. et al. Letters in Applied Microbiology. vol. 17, pp. 303–306, 1993.
Hashiba, H. et al. Biosci., Biotech., Biochem. vol. 56, No. 2, pp. 190–194, 1992.

Primary Examiner—James Ketter
Assistant Examiner—Irem Yucel
Attorney, Agent, or Firm—Darby & Darby

[57] ABSTRACT

Disclosed herein is a novel plasmid exhibiting high copy number and a plasmid vector obtained by modification of the plasmid.

7 Claims, 2 Drawing Sheets

PLASMID AND PLASMID VECTOR

BACKGROUND OF THE INVENTION

The present invention relates to a novel plasmid derived typically from *Lactobacillus helveticus*, and a novel plasmid vector which is prepared from the novel plasmid and which can be used for transformation of microorganisms, e.g. as a shuttle vector between *Lactobacillus helveticus* and other host.

*Lactobacillus helveticus* has been used for a long time as a typical dairy lactic acid bacteria starter for production of a fermented milk. It is known that one of the properties of *Lactobacillus helveticus* is strong proteolytic activity (Yamamoto, N., et al., Biosci. Biotech. Biochem., 58, 776–778 (1994)). Also, it has been reported that the fermented milk by *Lactobacillus helveticus* contains bioactive peptides which exhibit inhibitory effect against angiotensin converting enzyme which plays an important role in elevating blood pressure (Nakamura, Y. et al., J. Dairy Sci., 78, 777–783 (1995)), and the fermented milk by *Lactobacillus helveticus* has strong hypotensive effect due to these peptides (Nakamura, Y., et al., J. Dairy Sci., 78, 1253–1257 (1995)). As a method for effective utilization of strains having such properties, methods of genetic engineering utilizing genetic recombination techniques have conventionally been known. Although many plasmids for lactic acid bacteria have been reported, there are few reports on plasmids for lactic acid rod bacteria, Lactobacillus helveticus. Thus, there are few reports on host-vector system of *Lactobacillus helveticus*.

In order to perform genetic engineering by genetic recombination techniques, it is important to develop a vector suitable for an object strain, a transforming method having high transduction efficiency, and a host capable of holding the plasmid stably, i.e. a host-vector system. Particularly, if the copy number per host is insufficient, the productivity of effective substances becomes lower, which results in poor utility. In the case that the microorganisms themselves are ingested as a part of the fermented milk product, safety of the microorganisms employed for fermentation should be taken into account. However, safety of *Lactobacillus helveticus*, which has been used for fermented milk production for a long time, has been established by long eating experiences.

SUMMARY OF THE INVENTION

The object of the present invention is to provide a novel plasmid exhibiting high copy number derived from Lactobacillus lactic acid bacteria, typically *Lactobacillus helveticus*.

Another object of the present invention is to provide a novel plasmid vector obtained by modification of the aforementioned plasmid, which can be used as a shuttle vector.

The above and other objects of the present invention will become apparent more fully from the following description.

The inventor of the present invention surveyed the presence of plasmids in strains of *Lactobacillus helveticus* and measured the molecular weights thereof. As a result, the inventor found out from *Lactobacillus helveticus* CP53 strain a novel plasmid which is held stably and which exhibits high copy number, and obtained a useful plasmid vector with which transformation can be performed efficiently, by modifying the novel plasmid.

According to the present invention, there is provided a plasmid pCP53 having restriction sites as shown in FIG. 1 and having a length of about 11.5 kb.

According to the present invention, there is also provided a plasmid vector having a replication origin region of the plasmid pCP53, a replication origin region of a microorganism, and a marker gene.

According to the present invention, there is further provided a plasmid vector pCP53D having a replication origin region contained in a Hind III fragment of the aforementioned plasmid pCP53 having a length of about 2 kb, a replication origin region of pACYC177 derived from *Escherichia coli*, and a tetracycline resistance gene derived from *Streptococcus faecalis*; having restriction sites as shown in FIG. 2; and having a length of about 4.7 kb.

PREFERRED EMBODIMENT OF THE INVENTION

The present invention will now be explained in more detail hereunder.

Figure 1:
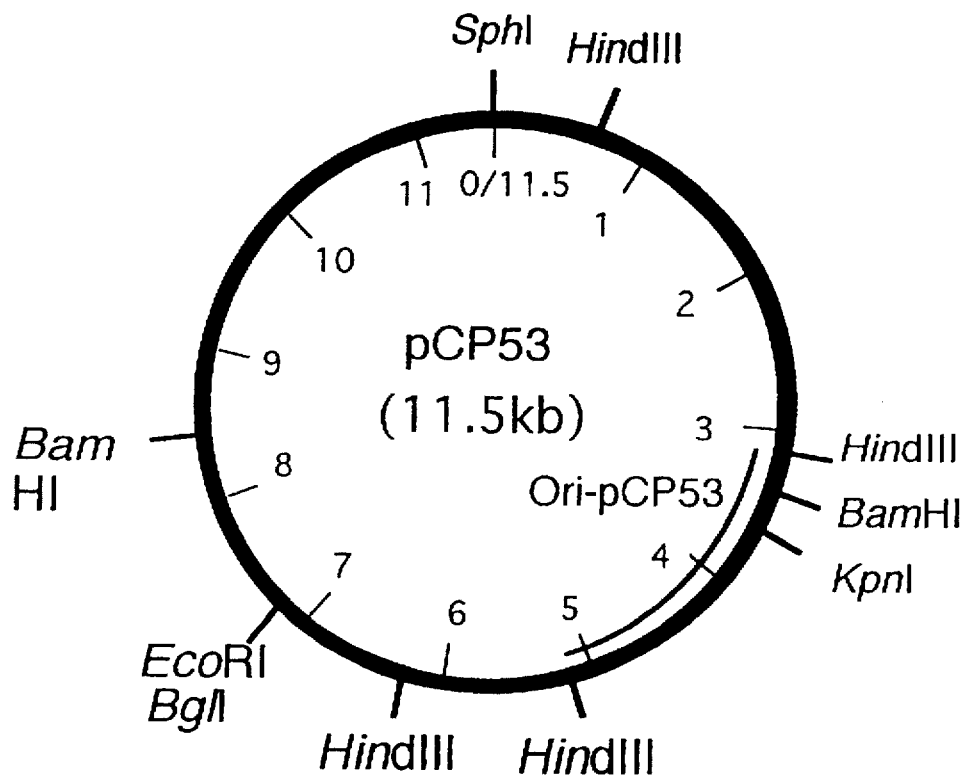
FIG. 1 is a restriction map of the plasmid pCP53 of the present invention.

The plasmid pCP53 of the present invention is a plasmid shown in FIG. 1 having a length of about 11.5 kb, and may be isolated from, e.g., *Lactobacillus helveticus* CP53 strain. *Lactobacillus helveticus* CP53 strain belongs to *Lactobacillus helveticus*, and was deposited at National Institute of Bioscience and Human-Technology Agency of Industrial Science and Technology on Jan. 11, 1996 and has been accorded accession number FERM BP-5770. FERM BP-5770 (1–3, Higashi 1 Ehome Tsukuba-shi, Ibaraki-ken 305, Japan), has been accepted for deposit under the Budapest Treaty on the International Recognition of the Deposit of Microorganisms for the Purposes of Patent Procedure. All restrictions on the availability to the public of FERM BP-5770 will be irrevocably removed upon the granting of a patent.

The CP53 strain has been obtained from the applicant's collection of strains, and has bacteriological properties as follows:

(Morphological Properties)
1) Shape of Cell; rod, 2) Motility; none, 3) Spore Formation; none, 4) Gram Stain; positive (Physiological Properties)
1) Catalase Production; negative, 2) Indole Production; negative, 3) Nitrate Reduction; negative, 4) Aerobic Growth; faculative anaerobic, 5) Formation of DL-lactic acid from glucose by homolactic fermentation without formation of gases
6) Carbohydrate degradation;
glucose: +,
maltose: −,
lactose: +,
cellobiose: −,
mannose: +,
trehalose: −,
fructose: +,
melibiose: −,
galactose: +,
raffinose: −,
sucrose: −,
stachyose: −,
mannitol: −, arabinose: –,
sorbitol: –,
xylose: –,
esculin: –,
rhamnose: –,
salicin: –

The plasmid pCP53 of the present invention may be replicated with high copy number in *Lactobacillus helveticus*, and collected with high yield. For example, when *Lactobacillus helveticus* CP53 strain having pCP53 is cultured overnight in MRS broth (manufactured by DIFCO LABORATORIES), about 1 μg of plasmid may be obtained per 1 ml of the medium.

The plasmid pCP53 of the present invention may be obtained by, e.g., culturing the aforementioned *Lactobacillus helveticus* CP53 strain, collecting cells after culturing, and isolating the plasmid by publicly known method such as agarose gel electrophoresis. The culturing may be performed in any mediums and conditions which are usually employed for culturing of this kind of microorganisms. Collecting of the cells may also be performed by publicly known procedures such as centrifugation. Cleavage by restriction enzymes and ligation by ligase of the plasmid pCP53 may be performed by the same procedures as those for publicly known plasmids.

Figure 2:
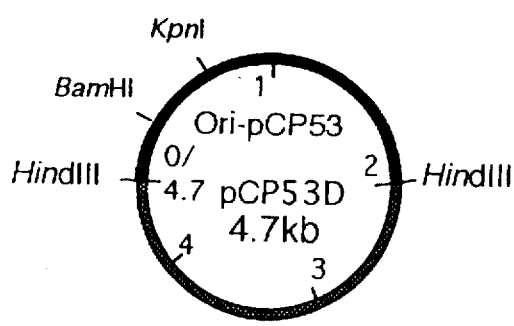
FIG. 2 is a restriction map of the plasmid vector pCP53D of the present invention.

The plasmid vector of the present invention is a vector in which a replication origin region of a microorganism and a marker gene is connected to a replication origin region of the plasmid pCP53, and may include, e.g., a plasmid vector pCP53D having a replication origin region contained in a Hind III fragment of the aforementioned plasmid pCP53 having a length of about 2 kb, a replication origin region of pACYC177 derived from *Escherichia coli*, and a tetracycline resistance gene derived from *Streptococcus faecalis;* having restriction sites as shown in FIG. 2; and having a length of about 4.7 kb.

The replication origin region of a microorganism may include, other than the replication origin region of pACYC177, a publicly known replication origin region of e.g. pBR322 and pBR329 derived from *Escherichia coli*. Further, replication origin regions such as pUB110,1 YEp24, pVA838 derived from *Bacillus subtilis* or yeast may also be used.

The marker gene may include drug resistance genes such as an ampicillin resistance gene, a tetracycline resistance gene and a chloramphenicol resistance gene, and enzyme producing genes derived from lactic acid bacteria or *Bacillus subtilis* which produce β-galactosidase or extracellular protease.

Figure 3:
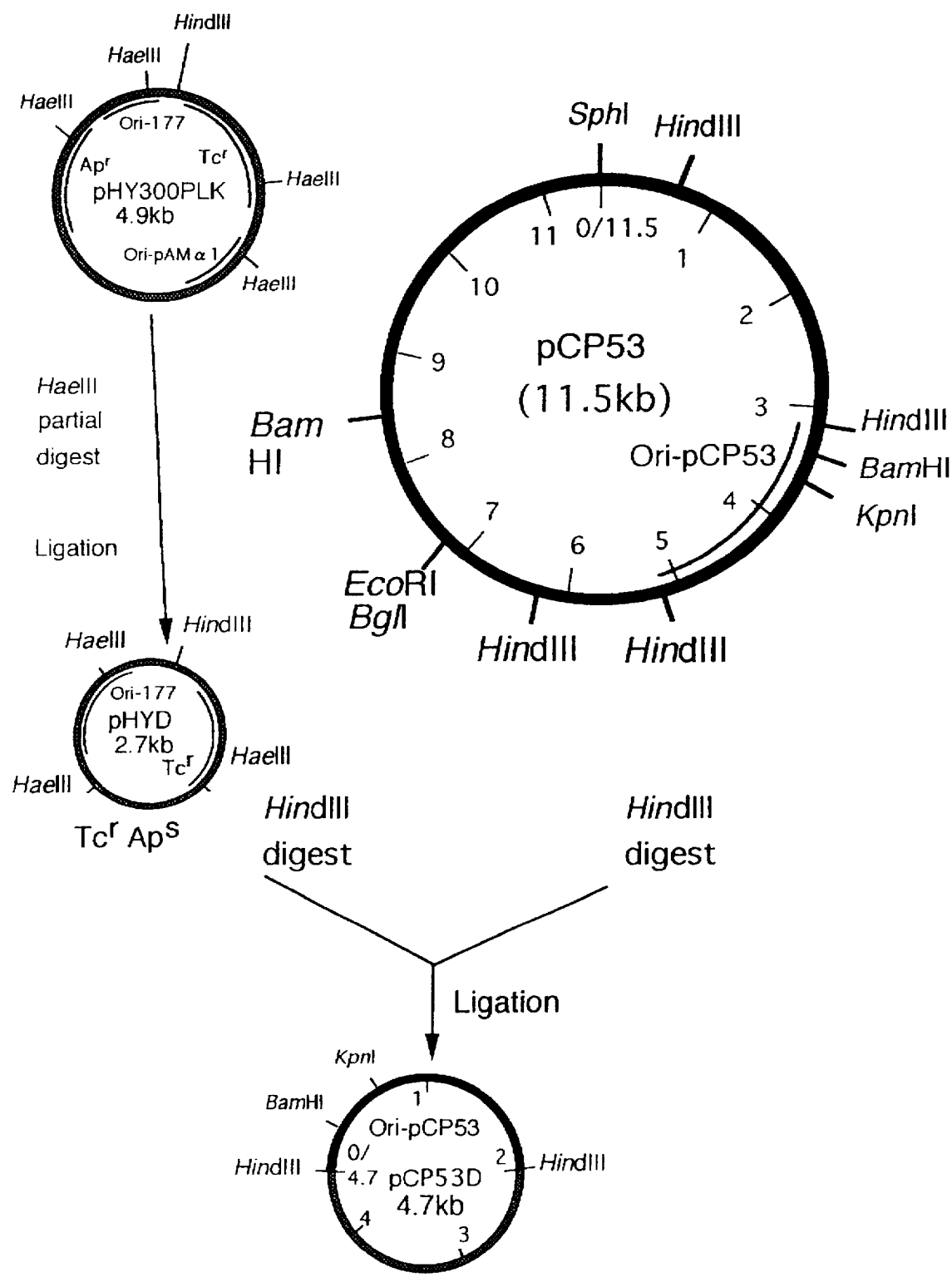
FIG. 3 illustrates a constructing process of the plasmid pCP53D of the present invention.

The aforementioned plasmid vector pCP53D may be obtained by connecting the replication origin region of a plasmid pACYC177 derived from *Escherichia coli* and a tetracycline resistance gene of a plasmid pAM α 1 derived from *Streptococcus faecalis*, to the plasmid pCP53 of the present invention, utilizing a plasmid pHY300PLK manufactured by TAKARA SHUZO CO., LTD. according to the procedure as shown in FIG. 3. Other plasmids shown in FIG. 3 than the plasmids of the present invention are publicly known and commercially available. The plasmid vector pCP53D may be used as a shuttle vector capable of being introduced into *Escherichia coli* and Lactobacillus lactic acid bacteria such as *Lactobacillus helveticus* and *Lactobacillus paracasei*.

The plasmid pCP53 of the present invention is held stably in *Lactobacillus helveticus* and replicated with high copy number. The plasmid vector pCP53D of the present invention is a useful shuttle vector with which transformation of *Lactobacillus helveticus* can be performed efficiently. Therefore, these are useful for genetic engineering of *Lactobacillus helveticus* utilizing genetic recombination techniques.

EXAMPLES OF THE INVENTION

The present invention will now be illustrated in more detail by way of Examples, but it is to be construed that the present invention is not limited by these Examples.

EXAMPLE 1

(Isolation of Plasmid)

GAM medium manufactured by NISSUI PHARMACEUTICAL CO., LTD. was inoculated with *Lactobacillus helveticus* CP53 strain, and cultured overnight at 37° C. After finishing culturing, cells were collected by centrifugation (10,000 rpm, 5 minutes). The cells were washed with 10 mM phosphate buffer—150 mM NaCl (pH 6.8), and the cells were collected by centrifugation under the above conditions.

Subsequently, purification of the plasmid was performed according to the following procedure. The collected cells were suspended in 0.2 ml of 25% sucrose and 10 mM tris-HCl buffer (pH 7.0) containing 10 mg/ml of lysozyme manufactured by SIGMA CHEMICAL CO., 1 mg/ml of N-acetylmuramidase manufactured by SEIKAGAKU CORP., and incubated at 37° C. for 30 minutes. The cell suspension was then admixed with 0.4 ml of 3% SDS-0.2N NaOH solution and allowed to stand at room temperature for about 5 minutes. The suspension was then further admixed with 0.3 ml of 3 M sodium acetate (pH 4.8) solution, allowed to stand on ice for 5 minutes, and centrifuged (15,000 rpm, 5 minutes) for collecting the supernatant. The supernatant was admixed with ethanol of twice the volume of the supernatant, and allowed to stand at −80° C. for 20 minutes. Subsequently, a precipitate was collected by centrifugation (15,000 rpm, 15 minutes), washed with 70% ethanol, dried, and then dissolved in 0.1 ml of 10 mM tris-HCl buffer-1 mM EDTA (pH 7.0), to obtain a roughly purified product of a plasmid. 1% agarose gel electrophoresis of the product was performed in order to confirm the presence of the plasmid and the molecular size thereof. For comparison, *Escherichia coli* HB101 strain having a plasmid pBR322 was cultured in LB medium (10 g of Bacto-tryptone, 5g of yeast extract, 10 of NaCl: pH 7.5), and the plasmid therefrom was purified and analyzed in the same manner as above, for comparing the collecting ratio. As a result, presence of the plasmid of *Lactobacillus helveticus* CP53 strain was confirmed with very high collecting ratio. The plasmid was named pCP53. The collecting amount of pCP53 was approximately 20% of that of the plasmid for *Escherichia coli*, pBR322 (1 μg/ml medium), which collecting ratio was very high for a *Lactobacillus helveticus* plasmid.

In order to locate restriction sites of pCP53, pCP53 was cleaved with nine sorts of six bases recognizing restriction enzymes, and fragments were analyzed by 1% agarose gel electrophoresis. As a result, it was confirmed that pCP53 has a molecular weight of 11.5 kb and has restriction sites shown in FIG. 1. Restriction sites of PstI, BglII or SalI were not recognized.

EXAMPLE 2

(Construction of Plasmid Vector pCP53D)

According to the operation procedure shown in FIG. 3, a plasmid vector having a replication origin region of the plasmid pCP53, a replication origin region of pACYC177 derived from *Escherichia coli*, and a tetracycline resistance gene derived from *Streptococcus faecalis* was constructed.

1) Construction of Vector for Searching Replication Origin Region

1 μg of plasmid pHY300PLK manufactured by TAKARA SHUZO CO., LTD. which has a replication origin region of pACYC177 derived from *Escherichia coli* (Ori-177), a replication origin region of a plasmid pAM α 1 derived from *Streptococcus faecalis* (Ori-pAM α 1), and an ampicillin resistance gene and a tetracycline resistance gene, was partially cleaved with HaeIII, and subjected to self-ligation by T4 DNA ligase. This DNA was transducted into *Escherichia coli* HB101 strain according to Maniatis' method (molecular cloning), and growable strain in LB agar medium containing 20 μg/ml of tetracycline was selected. As shown in FIG. 3, the strain transformed with pHY300PLK without the replication origin for Gram positive bacteria should become ampicillin sensitive. Thus, the growability of the above selected strains in LB agar medium containing 50 μg/ml of ampicillin was examined. From some ampicillin sensitive strains, plasmids therein were isolated according to the aforementioned method, and the restriction sites therein were examined. As a result, it was confirmed that pHYD (2.7 kb) shown in FIG. 3 had been constructed.

2) Cloning of the Replication Origin Region of pCP53 Plasmid

1 μg of the aforementioned PHYD, which is the vector for searching the Gram positive bacteria replication origin region, was cleaved with Hind III, whereas 1 μg of pCP53 was also cleaved with Hind III. These cleaved plasmids were mixed, and connected by T4 DNA ligase. This DNA was transducted into *Escherichia coli* HB101, and growable strains were selected in LB agar medium containing 20 μg/ml of tetracycline. The DNA obtained from the strain thus transformed was analyzed by 1% agarose gel electrophoresis. As a result, it was confirmed that various sizes of HindIII fragments which seemed to be derived from pCP53 were inserted into pHYD vector.

Subsequently, these various plasmids were introduced into Lactobacillus paracasei, and growable strains were screened in GAM medium containing 4 μg/ml of tetracycline. *Lactobacillus paracasei* JCM-8130 was cultured in GAM medium containing 1.5 mM of glycine at 37° C. for 20 hours. The medium was diluted ten times with a fresh GAM medium containing 1.5 mM of glycine, and culturing was further performed at 37° C. until the turbidity became 1.0. The cells were collected and washed with a buffer for electroporation (7 mM of HEPES, 272 mM of sucrose, 1 mM of MgCl$_2$,: pH 7.4). The cells were suspended in the buffer one twentieth the volume of the initial medium. 0.1 μg of each of the aforementioned plasmids and 0.1 ml of the suspended cells were mixed together, charged into a cuvette (0.1 cm cuvette) for GENE PULSER manufactured by BIB-RAD LABORATORIES and incubated for 30 minutes on ice. Electroporation was then performed with GENE PULSER under the condition of 4.0 kV/cm, 25 μF. The cells were diluted with GAM medium of 10 times the volume of the cells, incubated at 37° C. for one hour, and positive clone was selected in GAM agar medium containing 4 μg/ml of tetracycline. The plasmid in the transformed clone thus obtained was analyzed by 1% agarose gel electrophoresis. As a result, the presence of a plasmid of a length of 4.7 kb containing a 2 kb fragment of pCP53 was confirmed, which means that the 2.0 kb DNA fragment of pCP53 includes the replication origin region of pCP53 (Ori-pCP53). This vector being usable as a replicable shuttle vector for *Escherichia coli* or genus Lactobacillus was named pCP53D. On the other hand, tetracycline resistant transformed clone was not found among the cells having only pHYD (2.7 kb) which does not contain the 2.0 kb DNA fragment.

EXAMPLE 3

(Transformation of *Lactobacillus helveticus* strain with pCP53D)

Transformation of *Lactobacillus helveticus* CP611 strain with the aforementioned pCP53D was studied. *Lactobacillus helveticus* CP611 was deposited at National Institute of Bioscience and Human-Technology Agency of Industrial Science and Technology on Feb. 1, 1996 and has been accorded accession number FERM BP-5771. FERM BP-5771 has been accepted for deposit under the Budapest Treaty on the International Recognition of the Deposit of Microorganisms for the Purposes of Patent Procedure. All restrictions on the availability to the public of FERM BP-5771 will be irrevocably removed upon the granting of a patent.

*Lactobacillus helveticus* CP611 strain was cultured in GAM medium containing 1.5 mM of glycine at 37° C. for 20 hours. The medium was diluted ten times with a fresh GAM medium containing 1.5 mM of glycine, and culturing was further performed at 37° C. until the turbidity became 1.0. The cells were collected and washed with a buffer for electroporation (7 mM of HEPES, 272 mM of sucrose, 1 mM of MgCl$_2$,: pH 7.4). The cells were suspended in the buffer one twentieth the volume of the initial medium. 0.1 μg of pCP53D and 0.1 ml of the suspended cells were mixed together, and electroporation was then performed under the same conditions as above. The cells were diluted with GAM medium of 10 times the volume of the cells, incubated at 37° C. for one hour, and positive clone was selected in GAM agar medium containing 4 μg/ml of tetracycline. About six days later, transformed clones were obtained in the ratio of 500 cells/pg DNA. The transformed clones showed growability of 50% at tetracycline concentration of 10 μg/ml.

The plasmid in the transformed clone thus obtained was analyzed by 1% agarose gel electrophoresis. As a result, the presence of a plasmid of a length of 4.7 kb containing a 2 kb fragment of pCP53 was confirmed. Further, it is observed that the plasmid is held stably even after repeated passages. Thus, the vector was a useful shuttle vector for transformation of species *Lactobacillus helveticus*, and capable of transforming *Lactobacillus helveticus* CP611 efficiently.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An isolated plasmid PCP53 having restriction sites as shown in FIG. 1 and having a size of about 11.5 kb.

2. The plasmid as claimed in claim 1 wherein said plasmid is isolated from *Lactobacillus helveticus* CP53 (FERM BP-5770) strain.

3. The plasmid as claimed in claim 1 wherein said plasmid is isolated from *Lactobacillus helveticus* having bacteriological properties as follows:

(Morphological Properties)

1) Shape of Cell: rod, 2) Motility: none, 3) Spore Formation: none, 4) Gram Stain: positive;

(Physiological Properties)

1) Catalase Production: negative, 2) Indole Production: negative, 3) Nitrate Reduction: negative, 4) Aerobic Growth: facultative anaerobic, 5) Formation of DL-lactic acid from glucose by homolactic fermentation without formation of gases;

6) Carbohydrate degradation:
  glucose +;
  maltose: −;
  lactose: +;
  cellobiose: −;
  mannose: +;
  trehalose: −;
  fructose: +;
  melibiose: −;
  galactose: +;
  raffinose: −;
  sucrose: −;
  stachyose: −;
  mannitol: −;
  arabinose: −;
  sorbitol: −;
  xylose: −;
  esculin: −;
  rhamnose: −;
  salicin: −.

4. A plasmid vector having a replication origin region of the plasmid pCP53 in claim 1, a replication origin region of a microorganism, and a marker gene.

5. The plasmid vector as claimed in claim 4 wherein said vector has a replication origin region contained in an about 2 kb Hind III fragment of the plasmid pCP53 of claim 1, a replication origin region of pACYC177 obtained from *Escherichia coli*, and a tetracycline resistance gene obtained from *Streptococcus faecalis* as shown in FIG. 2; and has a size of about 4.7 kb.

6. The plasmid vector as claimed in claim 4 wherein said replication origin region of the microorganism is selected from the group consisting of the replication origin regions of pACYC177, pBR322, pBR329, pUB110, YEp24 and pVA838.

7. The plasmid vector as claimed in claim 4 wherein said marker gene is selected from the group consisting of an ampicillin resistance gene, a tetracycline resistance gene, a chloramphenicol resistance gene, a gene obtained from lactic acid bacteria which produces β-galactosidase, a gene obtained from lactic acid bacteria which produces extracellular protease, a gene obtained from *Bacillus subtilis* which produces β-galactosidase, and a gene obtained from *Bacillus subtilis* which produces extracellular protease.

* * * * *

UNITED STATES PATENT AND TRADEMARK OFFICE
CERTIFICATE OF CORRECTION

PATENT NO. : 5,766,940
DATED : June 16, 1998
INVENTOR(S) : Naoyuki YAMAMOTO

It is certified that error appears in the above-identified patent and that said Letters Patent is hereby corrected as shown below:

Title page, [75], Inventor, change "SAGMIHARA, JAPAN" to --KANAGAWA-KEN, JAPAN--.

Signed and Sealed this

Sixth Day of April, 1999

Attest:

Attesting Officer

Q. TODD DICKINSON

Acting Commissioner of Patents and Trademarks